US009687835B2

(12) United States Patent
Vos

(10) Patent No.: US 9,687,835 B2
(45) Date of Patent: Jun. 27, 2017

(54) COMPOSITION FOR IMPROVED NICKEL-LIGAND SOLUBILITY

(71) Applicant: INVISTA NORTH AMERICA S.A.R.L., Wilmington, DE (US)

(72) Inventor: Thomas E. Vos, Beaumont, TX (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 157 days.

(21) Appl. No.: 14/649,648

(22) PCT Filed: Dec. 6, 2013

(86) PCT No.: PCT/US2013/073688
§ 371 (c)(1),
(2) Date: Jun. 4, 2015

(87) PCT Pub. No.: WO2014/089492
PCT Pub. Date: Jun. 12, 2014

(65) Prior Publication Data
US 2015/0314280 A1  Nov. 5, 2015

Related U.S. Application Data

(60) Provisional application No. 61/734,520, filed on Dec. 7, 2012.

(51) Int. Cl.
*B01J 31/18* (2006.01)
*B01J 37/00* (2006.01)
*C07C 253/10* (2006.01)

(52) U.S. Cl.
CPC ............ *B01J 31/185* (2013.01); *B01J 37/00* (2013.01); *C07C 253/10* (2013.01); *B01J 2231/322* (2013.01); *B01J 2531/847* (2013.01); *B01J 2531/90* (2013.01)

(58) Field of Classification Search
None
See application file for complete search history.

(56) References Cited

U.S. PATENT DOCUMENTS

| | | | |
|---|---|---|---|
| 3,496,215 A | 2/1970 | Drinkard et al. |
| 3,496,217 A | 2/1970 | Drinkard et al. |
| 3,631,191 A | 12/1971 | Kane et al. |
| 3,655,723 A | 4/1972 | Drinkard |
| 3,766,237 A | 10/1973 | Squire et al. |
| 3,846,461 A | 11/1974 | Shook |
| 3,847,959 A | 11/1974 | Shook et al. |
| 3,903,120 A | 9/1975 | Shook et al. |
| 4,416,825 A | 11/1983 | Ostermaier |
| 5,512,696 A | 4/1996 | Kreutzer et al. |
| 5,723,641 A | 3/1998 | Tam et al. |
| 6,171,996 B1 | 1/2001 | Garner et al. |
| 7,659,422 B2 | 2/2010 | Foo et al. |
| 7,977,502 B2 | 7/2011 | Foo et al. |
| 8,088,943 B2 | 1/2012 | Foo et al. |
| 2009/0182163 A1* | 7/2009 | Foo ........................ B01J 31/185 558/338 |
| 2009/0182164 A1 | 7/2009 | Foo et al. |
| 2010/0267990 A1 | 10/2010 | Ritter et al. |
| 2011/0196168 A1 | 8/2011 | Ostermaier et al. |
| 2012/0035387 A1 | 2/2012 | Garner et al. |

FOREIGN PATENT DOCUMENTS

| | | |
|---|---|---|
| WO | 2008/008929 A2 | 1/2008 |
| WO | WO-2008008929 A2 | 1/2008 |
| WO | 2011/075494 A1 | 6/2011 |
| WO | 2011/075496 A1 | 6/2011 |
| WO | 2012/033556 A1 | 3/2012 |
| WO | WO-2014089492 A1 | 6/2014 |

OTHER PUBLICATIONS

Gothlich, et al., "Novel Chelating Phosphonite Ligands: Syntheses, Structures, and Nickel-Catalyzed-Hydrocyanation of Olefins," Organometallics, vol. 27, Issue 10, 2008, pp. 2189-2200.
Mallya, et al., "Studies on the Basic Carbonates of Nickel," Journal of the Indian Institute of Science, vol. 43, 1961, pp. 65-96.
International Search Report Received for PCT Application No. PCT/US2013/073688, mailed on Apr. 2, 2014, 4 pages.
International Preliminary Report on Patentability and Written Opinion Received for PCT Application No. PCT/US2013/073688, issued on Mar. 11, 2015, 11 pages.
Rhamdhani, et al., "Basic Nickel Carbonate: Part I. Microstructure and Phase Changes during Oxidation and Reduction Processes," Metallurgical and Materials Transactions B, vol. 39B, 2008, pp. 218-233.
Tolman, et al., "Homogeneous Nickel-Catalyzed Olefin Hydrocyanation," Advances in Catalysis, vol. 33, 1985, pp. 1-46.
"International Application Serial No. PCT/US2013/073688, International Search Report mailed Apr. 2, 2014", 4 pgs.

(Continued)

Primary Examiner — Joseph Kosack
(74) Attorney, Agent, or Firm — Robert B. Furr, Jr.

(57) ABSTRACT

In the hydrocyanation reaction of butadiene proceeding through pentenenitriles to adiponitrile, catalysis by complexes of zerovalent nickel with bidentate phosphorus-based ligands of the $NiL_2A$ type wherein $L_2$ is a bidentate ligand and A is an unsaturated compound, can be rate-limited by the solubility of the catalytic complex. The present invention concerns solvent compositions for the nickel-ligand complex comprising mixtures of unsaturated nitriles that provide for increased metal solubility, particularly in the absence of a Lewis acid promoter, resulting in higher hydrocyanation reaction rates in an industrial-scale process for production of important nylon manufacturing intermediates. The mixed nitrile solvent compositions can include mixtures of pentenenitriles and/or methylbutenenitriles. The mixtures of mixed unsaturated nitriles can be, at least in part, from recycle streams from the hydrocyanation reaction for which the nickel-bidentate ligand complexes are used as catalysts.

21 Claims, No Drawings

(56) References Cited

OTHER PUBLICATIONS

"International Application Serial No. PCT/US2013/073688, Written Opinion mailed Apr. 2, 2014", 6 pgs.
Alexander, Alexp, V Gothiich, et al., "Novel Chelating Phosphonite Ligands Syntheses, Structures, and Nickel-Catalyzed Hydrocyanation of Olefins", Organometallics, vol. 27, No. 10, (May 1, 2008), 2189-2200.

* cited by examiner

COMPOSITION FOR IMPROVED NICKEL-LIGAND SOLUBILITY

This application claims the priority of U.S. provisional application Ser. No. 61/734,520, filed Dec. 7, 2012, which is incorporated herein by reference in its entirety.

FIELD OF THE INVENTION

The invention relates to methods that can be used to produce catalyst nickel-ligand complexes with phosphorous-containing ligands by using compositions of the catalyst-forming reaction milieu that can provide greater solubility of the nickel-ligand complexes therein. Such catalyst solutions can be used in carrying out hydrocyanation reactions, such as hydrocyanation of 1,3-butadiene (BD) to form pentenenitrile (PN) and in the subsequent hydrocyanation of pentenenitrile to form adiponitrile (ADN), for the commercially important nylon synthesis field.

BACKGROUND OF THE INVENTION

Hydrocyanation catalyst systems useful for the hydrocyanation of ethylenically unsaturated compounds using transition metal complexes with monodentate phosphite ligands are documented in the prior art. See, for example, U.S. Pat. Nos. 3,496,215; 3,631,191; 3,655,723 and 3,766,237, and Tolman et al., Advances in Catalysis, 1985, 33, 1. The hydrocyanation of activated ethylenically unsaturated compounds, such as with conjugated ethylenically unsaturated compounds (e.g., BD and styrene), and strained ethylenically unsaturated compounds (e.g., norbornene) proceed without the use of a Lewis acid promoter, while hydrocyanation of unactivated ethylenically unsaturated compounds, such as 1-octene and 3-pentenenitrile (3PN), generally requires the use of a Lewis acid promoter. Recently, catalyst compositions and processes for the hydrocyanation of monoethylenically unsaturated compounds using zero-valent nickel and bidentate phosphite ligands in the presence of Lewis acid promoters have been described; for example in U.S. Pat. Nos. 5,512,696; 5,723,641; and 6,171,996.

U.S. Pat. No. 3,903,120 describes the preparation of zerovalent nickel complexes of the types $Ni(MZ_3)_4$ (i.e., $ML_4$ type) and $Ni(MZ_3)_2A$ (i.e. $ML_2A$ type); wherein M is P, As or Sb; Z is R or OR, wherein R is an alkyl or aryl radical having up to 18 carbon atoms and may be the same or different, and at least one Z is OR; A is a monoolefinic compound having 2 to 20 carbon atoms; the R radicals of a given $MZ_3$ of $Ni(MZ_3)_2A$ preferably being so chosen that the ligand has a cone angle of at least 130°; are prepared by reacting elemental nickel with the monodentate $MZ_3$ ligand at a temperature in the range of 0° C.-150° C. in the presence of a halogen-containing derivative of the monodentate $MZ_3$ ligand as a catalyst. A more rapid reaction is realized by carrying out the preparation in an organonitrile solvent. In comparison to monodentate phosphorus-containing ligands, bidentate phosphorus-containing ligands generally react more slowly with nickel metals described in the above references. Certain bidentate ligands, such as those that do not readily form $NiL_4$ complexes with nickel metal (i.e., do not form complexes with two moles of bidentate ligand per metal atom), will react more readily in the presence in the presence of Lewis acid promoters, such as $ZnCl_2$, forming higher concentrations of solubilized nickel, as its ligand complex, in the organic reaction milieu.

U.S. Pat. No. 4,416,825 also describes an improved, continuous process for the preparation of hydrocyanation catalysts comprising zerovalent nickel complexes with monodentate organophosphorus compounds (ligands) by controlling the temperature of the reaction relative to the amount of monodentate ligand and conducting the reaction in the presence of a chlorine ion and organic nitrile such as adiponitrile.

There are several processes that can be used to make nickel catalyst complexes with phosphorous-containing ligands. One method is a reaction between nickel bis(1,5-cyclooctadiene) $[NI(COD)_2]$ and a phosphite ligand; however, this process is not very economical because of the high costs of $Ni(COD)_2$. Another process involves the in situ reduction of anhydrous nickel chloride with zinc dust in the presence of the phosphite ligand. For this reaction to be successful, the nickel metal must react with the phosphorous-containing ligand at a sufficient rate to produce the nickel complex.

U.S. Pat. No. 6,171,996 describes zero-valent nickel complexes comprising bidentate phosphite ligands prepared or generated according to techniques well known in the art, as described, for example, in U.S. Pat. Nos. 3,496,217; 3,631,191; 3,846,461; 3,847,959; and 3,903,120. For example, divalent nickel compounds may be combined with a reducing agent, to serve as a source of zero-valent nickel in the reaction. Suitable divalent nickel compounds are said to include compounds of the formula $NiY_2$ where Y is halide, carboxylate, or acetylacetonate. Suitable reducing agents are said to include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120 is also a suitable source of zero-valent nickel. U.S. Pat. No. 8,088,943 also describes a zero-valent nickel complex comprising a bidentate phosphite ligand.

In comparison to monodentate phosphorus-containing ligands, bidentate phosphorus-containing ligands generally react more slowly with nickel metals described in the above references, and generally form metal complexes of the $NiL_2A$ (one mole of bidentate ligand per metal atom, plus unsaturated species A) rather than the $NiL_4$ type (2 moles of bidentate ligand per metal atom).

Many nickel salts can be converted to nickel metal by reduction with hydrogen at elevated temperatures. Potential sources are nickel oxide, nickel formate, nickel oxalate, nickel hydroxide, nickel carbonate, and basic nickel carbonate (BNC). BNC production has been disclosed by R. M. Mallya, et al. in the Journal of the Indian Institute of Science 1961, Vol. 43, pages 44-157 and M. A. Rhamdhani, et al., Metallurgical and Materials Transactions B 2008, Vol. 39B, pages 218-233 and 234-245.

One example of a suitable nickel metal is the INCO type 123 nickel metal powder (Chemical Abstract Service registry number 7440-02-0), derived from the decomposition of nickel carbonyl at elevated temperatures. A method of preparation of a nickel metal suitable for complex formation with phosphite ligand is disclosed in U.S. Published Patent Application No. 2011/0196168. Additional background on hydrocyanation and the adiponitrile (ADN) process is contained in U.S. Pat. No. 8,088,943 B2 and U.S. Pub No: US 2012/0035387 A1.

SUMMARY OF THE INVENTION

The present invention is directed, in various embodiments, to a composition of mixed unsaturated nitriles, which has unexpectedly been found to more effectively dissolve a catalytic complex of nickel metal with a bidentate phosphorus-containing ligand, compared to a composition including only a single unsaturated nitrile. The solubilized complex of the nickel metal and bidentate phosphorus-based ligand in the mixture of unsaturated nitriles is effective as a hydrocyanation catalyst, e.g., for production of adiponitrile (ADN). The complex of the nickel-bidentate phosphite ligand has unexpectedly been found to have higher solubility in the presence of mixed unsaturated nitriles, such as mixed pentenenitriles, than in milieu with only a single, pure, unsaturated nitrile, e.g., a single pentenenitrile. In various embodiments the invention is also directed to a catalytic solution of a nickel-ligand complex in the mixed unsaturated nitriles having a higher concentration of the active nickel catalyst than does a comparable art composition; to a method of preparing the catalytic solution with heightened levels of active nickel catalyst; and to methods of using the catalytic solution in the mixed nitrile solvent in carrying out hydrocyanation reactions.

Accordingly, the invention can provide a composition comprising a catalytic $ML_2A$-type nickel-ligand complex wherein M is nickel metal, $L_2$ is a single mole equivalent of a bidentate phosphorus-based ligand, and A is an unsaturated compound, dissolved in a solvent system comprising a mixture of unsaturated nitriles, the mixture comprising more than one pentenenitrile, more than one methylbutenenitrile, or a mixture of at least one pentenenitrile and at least one methylbutenenitrile. For example, A can be an unsaturated nitrile such as a pentenenitrile. For example, the composition can be free of a Lewis acid promoter; for example, the composition can be free of $ZnCl_2$.

The effect of the presence of unsaturated nitriles on the final nickel-ligand solubility is not seen with a monophosphite mixture of triaryl phosphites, which form $NiL_4$ complex species in solution. For bidentate ligands that are not able to make $NiL_4$ species due to the steric interactions (e.g., a tetra-coordinate Ni with two moles of bidentate ligands), the formation of a nickel-ligand complex, $L_2NiA$ (i.e., a lower coordinate Ni with a single mole of a bidentate ligand) is dependent on the unsaturated compounds A, that can also interact with the nickel. The amount of nickel in solution at the end of the reaction is a function of the amount of bidentate ligand and the type of other binding compounds in solution. The inventor herein has unexpectedly discovered that greater metal solubility is observed with a mixture of unsaturated nitriles is present. In the use of such a composition for catalysis of hydrocyanation reaction, the mixed unsaturated nitriles can come from a process as described in U.S. Pat. No. 8,088,943 B2 which has a mixed unsaturated nitrile stream flow to the catalyst reactor. Accordingly, the present invention can provide a hydrocyanation reaction milieu comprising the $ML_2A$ catalytic composition of the invention in a solvent system comprising a mixture of unsaturated nitriles, butadiene, and hydrogen cyanide contained in a reactor suitable for carrying out a hydrocyanation reaction, wherein the reaction milieu can be free of a Lewis acid promoter, such as zinc chloride or other metal chlorides. The milieu can be recharged during the reaction process with a catalytic $ML_2A$-type nickel-ligand complex wherein M is nickel metal, $L_2$ is a single mole equivalent of a bidentate phosphorus-based ligand, and A is an unsaturated compound, dissolved in a solvent system comprising a mixture of unsaturated nitriles, the mixture comprising more than one pentenenitrile, more than one methylbutenenitrile, or a mixture of at least one pentenenitrile and at least one methylbutenenitrile; wherein at least a portion of the solvent system comprising the mixture is from a recycle stream of the hydrocyanation reaction process.

The invention can also provide a method of preparing the composition of claim 1, comprising contacting nickel metal and a solution of a bidentate phosphorus-based ligand in a mixed unsaturated nitrile solvent system comprising more than one pentenenitrile, more than one methylbutenenitrile, or a mixture of at least one pentenenitrile and at least one methylbutenenitrile; wherein a concentration of the nickel-ligand complex dissolving in the mixed nitrile solvent composition is increased relative to a concentration of the nickel-ligand complex dissolving in a single nitrile solvent composition comprising a single pentenenitrile or a single methylbutenenitrile, under comparable conditions.

The invention can also provide a method of carrying out a hydrocyanation reaction, comprising contacting a hydrocyanation reaction substrate, hydrogen cyanide, and a catalytic $ML_2A$-type nickel-ligand complex wherein M is nickel metal, $L_2$ is a single mole equivalent of a bidentate phosphorus-based ligand, and A is an unsaturated compound, dissolved in a solvent system comprising a mixture of unsaturated nitriles, the mixture comprising more than one pentenenitrile, more than one methylbutenenitrile, or a mixture of at least one pentenenitrile and at least one methylbutenenitrile; e.g., in the absence of a Lewis acid promoter; under conditions suitable to bring about reaction of the substrate and the hydrogen cyanide. For example, the $ML_2A$-type nickel-ligand complex in a solvent system comprising a mixture of unsaturated nitriles can be prepared using a recycle stream from a hydrocyanation reaction.

DETAILED DESCRIPTION OF THE INVENTION

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The compound or set of compounds, such as are used in the inventive methods, can be any one of any of the combinations and/or sub-combinations of the elements as described herein.

A compound as shown in any of the Examples, or among the exemplary compounds, is provided.

Provisos can apply to any of the disclosed categories wherein any one or more of the other above disclosed categories or species can be excluded from such categories.

Aspects of the present disclosure employ, unless otherwise indicated, techniques of chemistry, and the like, which are within the skill of the art. Such techniques are explained fully in the literature. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

An "organic radical" or "organic group", as the term is used herein, refers to a portion or fragment or moiety, capable of bonding to another atom, wherein the group is carbon-based. By "carbon-based" is meant that at least a portion of the group comprises at least one carbon atom, which can be covalently bonded to other atoms capable of covalent bonding such as hydrogen, nitrogen, oxygen, halogen, sulfur, phosphorus, and the like, as is well known in the art.

When a group, e.g., an "alkyl" group or an "aryl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded.

Standard abbreviations for chemical groups such as are well known in the art can be used herein, and are within ordinary knowledge; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl of R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

Substituent groups J can independently be halo, nitro, cyano, OR, NR$_2$, or R, or is C(O)OR, C(O)NR$_2$, OC(O)OR, OC(O)NR$_2$, N(R)C(O)OR, N(R)C(O)NR$_2$ or thio/thiono analogs thereof. By "thio/thiono analogs thereof", with respect to a group containing an O, is meant that any or all O atoms in the group can be replaced by an S atom; e.g., for group C(O)OR, a "thio/thiono analog thereof" includes C(S)OR, C(O)SR, and C(S)SR; e.g., for group OC(O)NR$_2$, a "thio/thiono analog thereof" includes SC(O)NR$_2$, OC(S)NR$_2$, and SC(S)NR$_2$; and so forth.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group.

When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

Alkyl groups include straight chain and branched alkyl groups and cycloalkyl groups having from 1 to about 20 carbon atoms, and typically from 1 to 12 carbons or, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. The cycloalkyl group can have 3 to about 8-12 ring members, or, the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. Aryl groups can contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above. Aryl groups can also bear fused rings, such as fused cycloalkyl rings, within the meaning herein. For example, a tetrahydronaphthyl ring is an example of an aryl group within the meaning herein. Accordingly, an aryl ring includes, for example, a partially hydrogenated system, which can be unsubstituted or substituted, and includes one or more aryl rings substituted with groups such as alkyl, alkoxyl, cycloalkyl, cycloalkoxyl, cycloalkylalkyl, cycloalkoxyalkyl, and the like, and also fused with, e.g., a cycloalkyl ring.

A "pentenenitrile" as the term is used herein refers to linear 5-carbon unsaturated nitriles of all possible stereochemistries, and mixtures thereof. Accordingly, hydrocyanation of butadiene (BD) to yield pentenenitrile (PN) is understood to provide one or more pentenenitrile isomers, such as cis or trans 2-pentenenitrile, 3-pentenenitrile, 4-pentenenitrile, or mixtures thereof. Hydrocyanation of BD can also yield the unwanted byproduct 2-methyl-3-butenenitrile (2M3BN). Isomerization of 2M3BN to PN refers to the rearrangement of the branched chain unsaturated nitrile to the linear unsaturated nitrile.

A "ligand" as the term is used herein refers to a neutral phosphorus-containing organic molecule that can complex a metal atom such as nickel to provide a metal-ligand complex. In the case of nickel complexes with ligands of this type, as described further below, the nickel can be complexed by four phosphorus atom ($ML_4$ type complex), wherein the four complexing phosphorus atoms can be made up by four molecules of a monodentate ligand (each ligand molecule thus containing a single metal-complexing phosphorus atom), or by two molecules of a bidentate ligand (each ligand molecule thus containing two each metal-complexing phosphorus atoms). In other complexes, especially with bulky bidentate ligands, the nickel metal atom can only accommodate two complexing phosphorus atoms, but may be able to be bound to another ligand as well, such as an unsaturated compound. These complexes, referred to as $ML_2A$ or $NiL_2A$ (specifically for nickel) complexes, thus comprise a central nickel atom coordinated by the two phosphorus atoms of a single molecule of a bidentate ligand (or two molecules of a monodentate ligand), in addition to another ligand comprising an unsaturated compound (containing a π-bond), such as an unsaturated nitrile (e.g., 3-pentenenitrile, etc.). The metal-solubilizing compositions and methods as disclosed and claimed herein relate to catalytic complexes of the $ML_2A$ type.

Phosphorus-Based Ligand for Hydrocyanation Catalysts

Complexes of nickel metal with phosphorus-based ligands, such as nickel complexes with a bidentate ligand of formula (V):

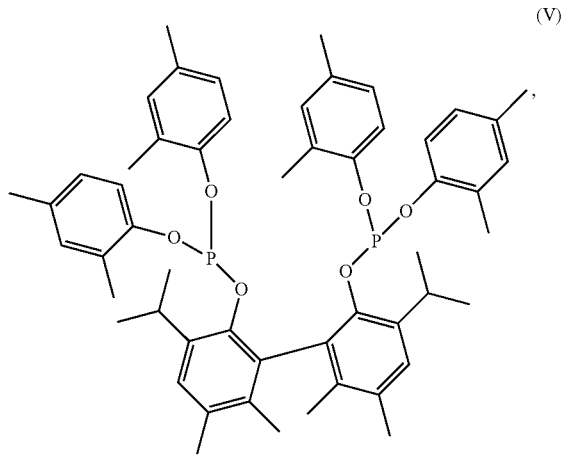

(V)

or of formula (XIII):

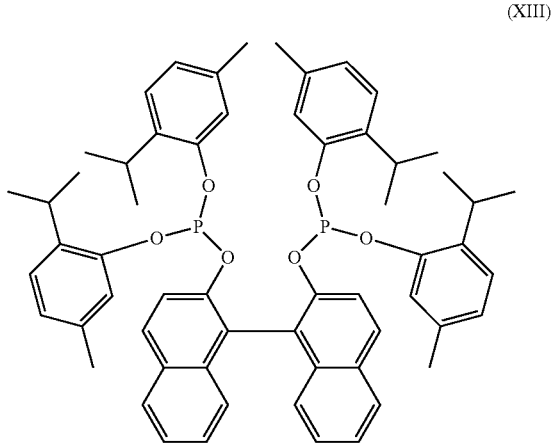 [SMILES: Cc1ccc(C(C)C)c(OP(Oc2cc(C)ccc2C(C)C)Oc2ccc3ccccc3c2-c2c(OP(Oc3cc(C)ccc3C(C)C)Oc3cc(C)ccc3C(C)C)ccc3ccccc23)c1]

(XIII)

are homogeneous catalysts used in reaction milieu for hydrocyanation reactions, such as the hydrocyanation of butadiene in the manufacture of adiponitrile. Other bidentate ligands can be also used in compositions and methods of the present invention, which are detailed below. Bidentate ligands often form complexes of the $NiL_2A$ ($ML_2A$) type, rather than the $NiL_4$ ($ML_4$) type, which can be due to the steric bulk of the bidentate ligand around the metal atom. In a nickel complex with a ligand of formula (V) or of formulas (XIII), a $ML_2A$ complex comprises one molecule of ligand (V) or (XIII) respectively per nickel metal atom, with additional coordination for the nickel metal atom being provided by unsaturated compound A, which can be an unsaturated nitrile such as a pentenenitrile (PN), (e.g., 3-pentenenitrile, cis or trans), a 2-methyl-3-butenenitrile (2M3BN), or the like, or can be butadiene or another unsaturated organic compound, i.e., as a substrate for a hydrocyanation reaction catalyzed by the metal complex.

The solubility of the nickel-ligand complex in the hydrocyanation reaction milieu can be a limiting factor in the overall rate of the hydrocyanation reaction, as the catalytic metal-ligand complex should be homogeneously dissolved in the reaction milieu to effectively catalyze the hydrocyanation of butadiene to an unsaturated nitrile, or the hydrocyanation of the unsaturated nitrile to adiponitrile. The inventor herein has surprisingly found that mixtures of unsaturated nitriles can be better solvents for the nickel-ligand complex than are solvents comprising a single unsaturated nitrile, even when a Lewis acid promoter is absent. Accordingly, in various embodiments, the invention provides methods and compositions in which mixtures of unsaturated nitriles, i.e. stream 5 and/or stream 11 and/or stream 12 as defined in U.S. Pat. No. 8,088,943, can effectively dissolve catalytic nickel-ligand complexes, such as complexes of nickel metal and ligand (V), at higher concentrations than could be achieved using single-component solvent systems. The higher solubility of the catalyst can result in higher effective rates and throughputs for hydrocyanation products of value such as adiponitrile in industrial scale processes.

Organophosphorus compounds useful as phosphorus-based ligands for metals such as nickel include molecular entities wherein one or more phosphorus atoms is present, and one or more organic radicals or moieties is also present. An organophosphorus compound can further include other elements such as oxygen, halogens, hydrogen, nitrogen, and the like. Some terms in common usage for various classes of organophosphorus compounds, wherein P is a phosphorus atom and R indicates an organic moiety that is bonded via a carbon-phosphorus bond to the phosphorus atom, include "phosphine" ($PR_3$), "phosphine oxide" ($P(O)R_3$), "phosphinite" ($P(OR)R_2$), "phosphonite" ($P(OR)_2R$), "phosphinate" ($ROP(O)R_2$), "phosphite" ($P(OR)_3$), "phosphonate" ($RP(O)(OR)_2$), and "phosphate" ($P(O)(OR)_3$).

A "phosphorus-based ligand" as the term is used herein refers to a ligand containing at least one phosphorus atom, that is suitable for formation of a complex with a transition metal such as nickel, wherein the complex can possess catalytic activity for an organic reaction such as a hydrocyanation reaction of an olefin, such as the hydrocyanation of butadiene to yield pentenenitrile, or the hydrocyanation of pentenenitrile to yield adiponitrile. The term "phosphorus-based" refers to an organic compound that contains at least one phosphorus atom, whether or not it has catalytic activity.

A phosphorus-based ligand containing at least one phosphite ester bond can be a component of a hydrocyanation catalyst, such as when combined with a transition metal, e.g., nickel, as is known in the art. The metal, such as nickel, can be zero-valent, i.e., in metallic form. Reaction of the metal with the ligand can make the complex soluble in certain organic solvents. The ligand can be, for example, a phosphite, a phosphonite, a phosphinite, a phosphine, or a mixed phosphorus-based ligand or a combination of such members, provided the ligand contains at least one hydrolyzable P—O—C bond, wherein P is a phosphorus atom (which additionally bears other substituents), O is an oxygen atom, and C represent an organic radical, such as an aryl group, as described herein.

In general, a phosphorus-based ligand can be monodentate or multidentate, for example, bidentate or tridentate. The term "monodentate" is well known in the art, and means that each molecule of the ligand possesses a single phosphorus atom, which can be bonded to a single metal atom. The term "bidentate" is well known in the art, and means that each molecule of the ligand possesses two phosphorus atoms (e.g., a compound of formula (III)), and both phosphorus atoms of the ligand can be bonded to a single metal atom. A bidentate ligand is also known in the art as a chelate ligand. The compositions and methods of the present invention relate to nickel complexes with bidentate ligands of the $ML_2A$ type.

As used herein, the term "mixed phosphorus-based ligand" means a phosphorus-based ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members, provided that there is at least one P—O—C bond, wherein P is a phosphorus atom, O is an oxygen atom, and C represent an organic radical, such as an aryl group, that is subject to hydrolysis under acid catalysis.

Suitable phosphorus-based ligands for the transition metal, e.g., nickel, complex, can be selected from the group consisting of bidentate ligands of formula (III)

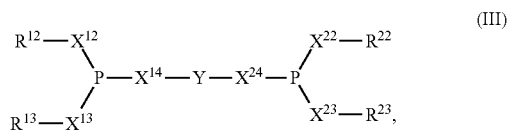

(III)

wherein $X^{12}$, $X^{13}$, $X^{14}$, $X^{22}$, $X^{23}$, and $X^{24}$, each independently is oxygen or a bond, provided that at least one of $X^{12}$, $X^{13}$, $X^{14}$, $X^{22}$, $X^{23}$, or $X^{24}$ is oxygen;

$R^{12}$, $R^{13}$, $R^{22}$, and $R^{23}$, each independently is (C1-C10) alkyl, (C3-C10)cycloalkyl, (C3-C10)cycloalkyl(C1-C10) alkyl, (C6-C20)aryl, or (C6-C20)aryl(C1-C10)alkyl, wherein for any (C6-C20)aryl or (C6-C20)aryl(C1-C10) alkyl of $R^{12}$, $R^{13}$, $R^{22}$, or $R^{23}$, each ring thereof is unsubstituted or is substituted with 1-4 substituents independently selected from the group consisting of (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy (C1-C10)alkyl, (C3-C10)cycloalkyl(C1-C10)alkoxy, (C3-C10)cycloalkoxy(C1-C10)alkoxy, (C6-C20)aryl, and (C6-C20)aryl(C1-C10)alkyl; or, optionally, one or more of pairs $R^{12}$ and $R^{13}$ or $R^{22}$ and $R^{23}$ are mutually directly bonded, such that the $R^{12}X^{12}$ and $R^{13}X^{13}$ groups, or the $R^{22}X^{22}$ and $R^{23}X^{23}$ groups, or both, together with the respective phosphorus atom to which each pair of groups is bonded, forms a respective ring; and, Y is an (C6-C20)arylene group, wherein each ring thereof is independently unsubstituted or is substituted with 1-4 (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, (C3-C10)cycloalkoxy(C1-C10)alkoxy, (C6-C20)aryl, (C6-C20)aryl(C1-C10)alkyl, fluorine, chlorine, bromine, or (C1-C10)haloalkyl.

An example of a bidentate phosphite ligand that is useful in the present process, i.e., a compound of formula (III), above, is a ligand having formula (V), shown below:

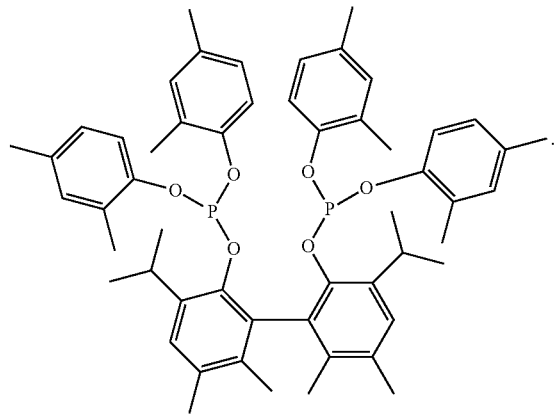

(V)

Another example is a ligand of formula (XIII):

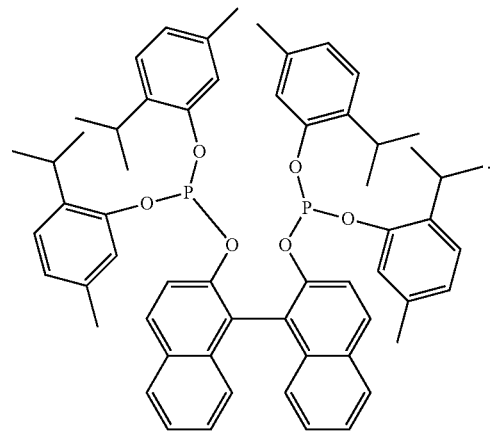

(XIII)

The use of these ligands is described in greater detail below.

Further examples of bidentate phosphite ligands that are useful in the present process include those having the formulas (VI) to (IX), shown below wherein for each formula, $R^{17}$ can selected from the group consisting of methyl, ethyl and isopropyl, and $R^{18}$ and $R^{19}$ can be independently selected from H and methyl. Or, each of $R^{17}$, $R^{18}$, and $R^{19}$ can independently be a higher alkyl, cycloalkyl, alkoxyl, or cycloalkoxyl.

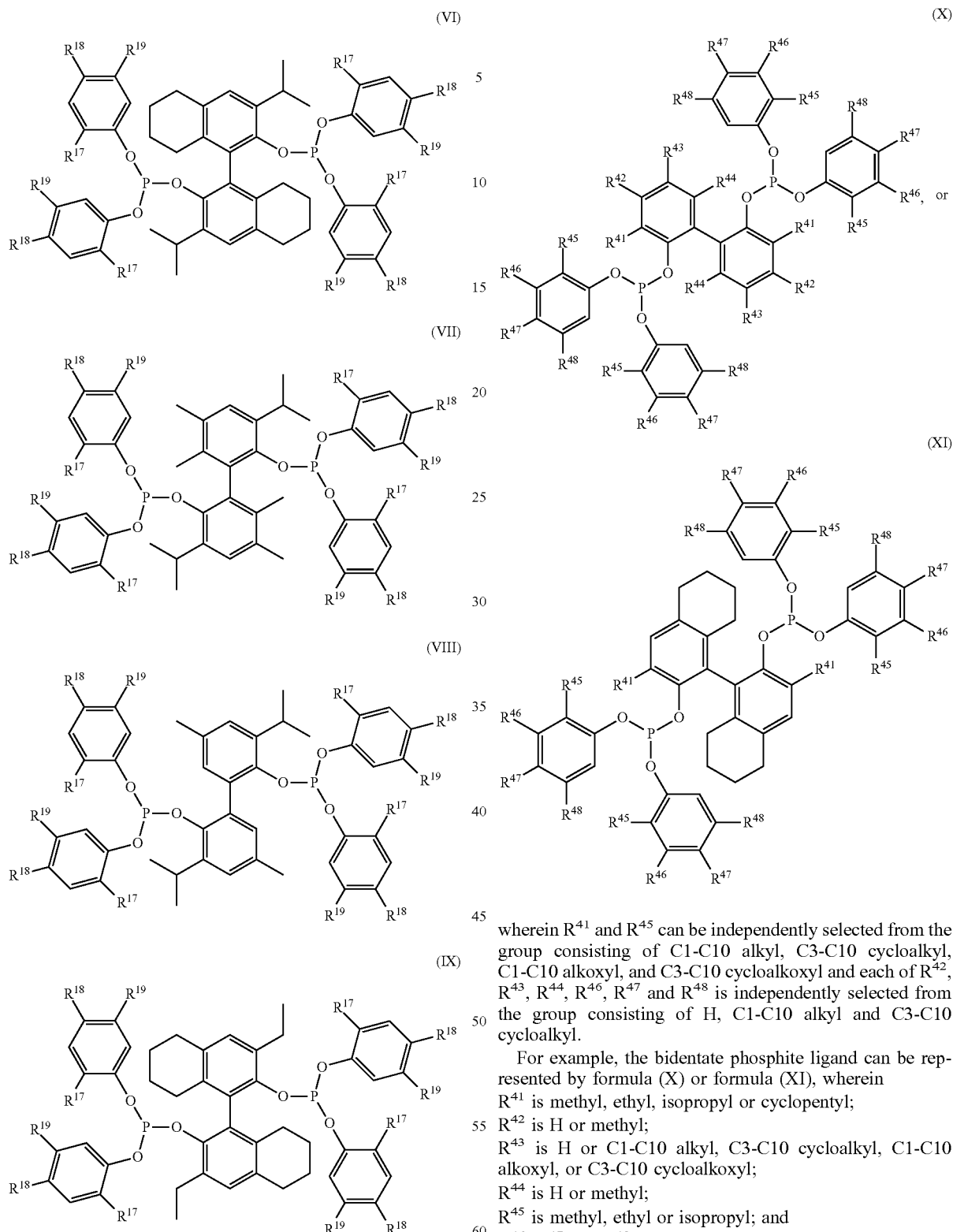

Additional examples of bidentate phosphite ligands that are useful in the present process include a ligand selected from a member of the group represented by formulas (X) and (XI), in which all like reference characters have the same meaning, except as further explicitly limited:

wherein $R^{41}$ and $R^{45}$ can be independently selected from the group consisting of C1-C10 alkyl, C3-C10 cycloalkyl, C1-C10 alkoxyl, and C3-C10 cycloalkoxyl and each of $R^{42}$, $R^{43}$, $R^{44}$, $R^{46}$, $R^{47}$ and $R^{48}$ is independently selected from the group consisting of H, C1-C10 alkyl and C3-C10 cycloalkyl.

For example, the bidentate phosphite ligand can be represented by formula (X) or formula (XI), wherein
$R^{41}$ is methyl, ethyl, isopropyl or cyclopentyl;
$R^{42}$ is H or methyl;
$R^{43}$ is H or C1-C10 alkyl, C3-C10 cycloalkyl, C1-C10 alkoxyl, or C3-C10 cycloalkoxyl;
$R^{44}$ is H or methyl;
$R^{45}$ is methyl, ethyl or isopropyl; and
$R^{46}$, $R^{47}$ and $R^{48}$ are each independently selected from the group consisting of H, C1-C10 alkyl, C3-C10 cycloalkyl, C1-C10 alkoxyl, and C3-C10 cycloalkoxyl.

For example, the bidentate phosphite ligand can be represented by formula (X) or (XI), wherein
$R^{41}$, $R^{44}$, and $R^{45}$ are methyl;
$R^{42}$, $R^{46}$, $R^{47}$ and $R^{48}$ are H; and, $R^{43}$ is a C1-C10 alkyl, C3-C10 cycloalkyl, C1-C10 alkoxyl, or C3-C10 cycloalkoxyl;

or, by the formula (X) or (XI), wherein $R^{41}$ is isopropyl;

$R^{42}$ is H;

$R^{43}$ is C1-C10 alkyl, C3-C10 cycloalkyl, C1-C10 alkoxyl, or C3-C10 cycloalkoxyl;

$R^{44}$ is H or methyl;

$R^{45}$ is methyl or ethyl;

$R^{46}$ and $R^{48}$ are each independently H or methyl; and $R^{47}$ is H, methyl or t-butyl.

Alternatively, the bidentate phosphite ligand can be represented by formula (X) or (XI), wherein $R^{41}$ is isopropyl or cyclopentyl;

$R^{45}$ is methyl or isopropyl; and $R^{46}$, $R^{47}$, and $R^{48}$ are H.

As yet another example, the bidentate phosphite ligand can be represented by Formula (X) or (XI), wherein $R^{41}$ is isopropyl; $R^{42}$, $R^{46}$, and $R^{48}$ are H; and $R^{43}$, $R^{44}$, $R^{45}$, and $R^{47}$ are methyl.

As another example, the ligand of formula (III) can be of formula (XII):

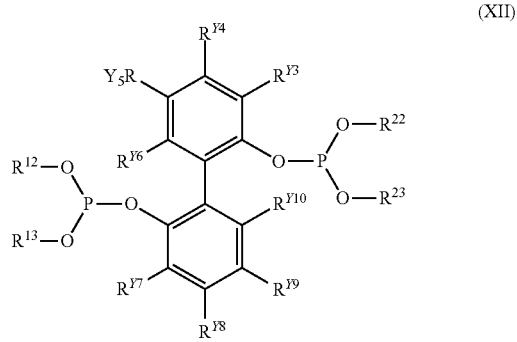

(XII)

wherein each of $R^{12}$, $R^{13}$, $R^{22}$ and $R^{23}$ is independently an unsubstituted or a substituted monovalent aryl, and each of $R^{Y3}$-$R^{Y10}$ is independently selected from the group consisting of hydrogen, (C1-C10) alkyl, and (C1-C10)alkoxy; or wherein two adjacent groups comprising any of $R^{Y3}$-$R^{Y10}$ together form an optionally substituted fused aryl ring. By a "monovalent aryl" group is meant an aryl group, which can be otherwise unsubstituted or substituted, bonded not more than one phosphite group. By an "optionally substituted fused aryl ring" is meant that any adjacent pair of $R^{Y3}$-$R^{Y10}$ can, together with the atoms of the ring to which they are bonded, themselves form another aryl ring which can be unsubstituted or substituted.

More specifically, for example, for a ligand of formula (XII), $R^{12}$, $R^{13}$, $R^{22}$, and $R^{23}$ are each independently phenyl substituted at a respective single ortho-position with a (C1-C10)alkyl or (C1-C10)alkoxy, wherein respective meta- and para-positions of the $R^{12}$, $R^{13}$, $R^{22}$, and $R^{23}$ phenyls can each independently be unsubstituted or be independently substituted with (C1-C10)alkyl, (C3-C10)cycloalkyl, (C1-C10)alkoxy, (C3-C10)cycloalkoxy, (C3-C10)cycloalkyl(C1-C10)alkyl, (C3-C10)cycloalkoxy(C1-C10)alkyl, (C3-C10)cycloalkyl(C1-C10)alkoxy, or (C3-C10)cycloalkoxy(C1-C10)alkoxy;

$R^{Y6}$ and $R^{Y10}$ are independently (C1-C10)alkyl or (C1-C10)alkoxy, and $R^{Y3}$, $R^{Y4}$, $R^{Y5}$, $R^{Y7}$, $R^{Y8}$, and $R^{Y9}$, are independently H, (C1-C10)alkyl, or (C1-C10)alkoxy, provided that at least one of $R^{Y3}$, $R^{Y4}$, or $R^{Y5}$, and at least one of $R^{Y7}$, $R^{Y8}$, or $R^{Y9}$, is (C1-C10)alkyl or (C1-C10)alkoxy.

It will be recognized that Formulas (V) to (XIII) are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulas (V) to (XIII), respectively, can bring the two phosphorus atoms of each Formula in closer proximity to one another and can allow the phosphite ligand to bind to nickel in a bidentate fashion. In addition, use of an optically active moiety such as sec-butyl for $R^{41}$ can result in optically active catalysts.

Hydrocyanation of Butadiene

The hydrocyanation of BD to yield ADN directly or indirectly through isomerization and/or additional hydrocyanation of intermediates with modern phosphorus-containing catalysts set forth below is well known in the art as evidenced by U.S. Pat. Nos. 7,977,502; 7,659,422; and U.S. Published Applications 2009/0182164 and 2010/0267990. Various modifications can be used alone or in combination to achieve the desired efficiency with the selected components of the reaction. Thus, separation steps, temperatures, refining, distillation, isomerization zones, pressures, elimination of constituents along the pathway, column sizes and configurations, stream velocities, recycling, and other process variables can be adjusted to modify the overall ADN production as required.

The catalyst composition can be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, a mixture of isomeric pentenenitriles, a mixture of isomeric methylbutenenitriles, a mixture of isomeric pentenenitriles and isomeric methylbutenenitriles, or the reaction product from a previous reaction campaign, can be used to dissolve to the catalyst composition.

The HCN-containing feed, the BD-containing feed, and the catalyst composition are contacted in a reaction zone which can be contained in any suitable equipment known to one skilled in the art. One or more pieces of conventional equipment can be used to provide the reaction zone, for example continuous stirred-tank reactors, loop-type bubble column reactors, gas circulation reactors, bubble column reactors, tubular reactors, or combinations thereof, optionally with apparatus for removing at least a portion of the heat of reaction.

The reaction temperature is typically maintained within the range of about 80° C. to about 140° C., for example within the range of about 100° C. to about 130° C. Generally, the reaction pressure should be sufficient to maintain the reagents in the liquid state, with such pressure at least, in part, a function of the amount of unreacted BD present in the reaction mixture.

Though the invention is not limited by an upper limit of pressure, for practical purposes the pressure generally ranges from about 15 psia to about 300 psia (about 103 kPa to about 30 2068 kPa).

HCN, substantially free of carbon monoxide, oxygen, ammonia, and water can be introduced to the reaction as a vapor, liquid, or mixtures thereof. As an alternative, cyanohydrins can be used as the source of HCN. See, for example, U.S. Pat. No. 3,655,723.

The molar ratio of the HCN in the feed to the BD in the feed is in the range of about 0.90:1.00 to about 1.04:1.00, for example in the range of about 0.92:1.00 to about 0.98:1.00.

This range of molar ratios can be advantageous over those 40 with a significantly larger excess of BD to HCN in that there can be less unreacted BD to recover and recycle to the process, and yield losses to 2-methylglutaronitrile (MGN) and to BD dimers, oligomers, and related species can be reduced. The molar ratio of the zero-valent nickel in the feed to the BD in the feed is in the range of about 0.00005:1.00 to about 0.0050:1.00, for example in the range about 0.0001:1.00 to about 0.0010:1.00.

The residence time in the reaction zone (for example, the time necessary for the combined feeds to displace one reactor so volume in a continuous-stirred-tank-reactor (CSTR) is typically determined by the desire to maintain the 2M3BN concentration below about 15 weight percent of the total mass of the reaction mixture, for example at or below about 10 weight percent of the total mass of the reaction mixture, and is also related to the catalyst concentration and reaction temperature. Generally residence times will be in the range of about 0.5 to about 15 hours, for example in the range of about 1 to about 10 hours.

Lewis Acid Promoter

A reaction for hydrocyanating 3-pentenenitrile to produce adiponitrile can take place in the presence of a promoter for promoting this reaction, such as a Lewis acid, such as an inorganic compound, an organometallic compound, or combinations thereof. Typically in hydrocyanation reactions, a cation or electron-accepting atom of the Lewis acid is selected from the group consisting of scandium, titanium, vanadium, chromium, manganese, iron, cobalt, copper, zinc, boron, aluminum, yttrium, zirconium, niobium, molybdenum, cadmium, rhenium, lanthanum, erbium, ytterbium, samarium, tantalum, and tin. However, the reactions, such as those reactions which take place in the first reaction zone for hydrocyanating 1,3-butadiene and the second reaction zone for isomerizing 2-methyl-3-butenenitrile, preferably can take place in the absence or substantial absence of such a promoter. More specifically, the reactions can take place in the absence of a Lewis acid promoter such as in the absence of $ZnCl_2$.

Dinitriles can be produced in the first reaction zone by the reaction of 3-pentenenitrile (3PN) or 2-methyl-3-butenenitrile (2M3BN) with HCN. Lewis acids are capable of promoting the formation of dinitriles in the first reaction zone, but in an embodiment of the present invention, Lewis acids are preferably not introduced into the first reaction zone in detectable amounts.

Lewis acid can be unintentionally introduced into the first reaction zone as a result of a unit upset or operator error. However, the continuous production of 3-pentenenitrile can be maintained using a method of the invention, provided that the ratio of atomic equivalents of Ni to moles of Lewis Acid in the first reaction zone is less than 10:1 during the course of at least 95% of the production of 3-pentenenitrile.

Use of Mixed Nitrile Solvents to Increase Catalyst Solubility

In U.S. Patent Application Publication Number 2011/0196168, incorporated by reference herein in its entirety, it is described that in formation of a solution of a nickel complex with a bidentate phosphorus-based ligand (e.g., a triarylphosphite such as ligand (V)), the reaction mixture may further comprise an organonitrile selected from one or more members of the group consisting of 2-pentenenitrile, 3-pentenenitrile, 4-pentenenitrile, 2-methyl-3-butenenitrile, 2-methyl-2-bytenenitrile, adiponitrile, 2-methylglutaronitrile, and ethylsuccinotrile. The '168 application further describes that making the nickel complex or nickel complexes from the reaction of monodentate and bidentate ligands with the nickel-containing solids of this invention can be performed as described in therein; for example, a 5 wt % solution of a bidentate phosphorus-containing ligand in pentenenitrile solvent further comprising a Lewis acid like $ZnCl_2$ (0.5 to 2.5 moles Lewis acid per mole bidentate phosphorus-containing ligand) can be contacted with the nickel-containing solid of the invention (for example, 4.0 wt % nickel-containing solid). Temperatures between 60° C. and 80° C. gave acceptable reaction rates. The '168 application discloses that additional $ZnCl_2$ would promote higher nickel catalyst concentrations, but this is not preferred, due to higher amount of $ZnCl_2$ used in the process for pentenenitrile hydrocyanation since liquid-liquid extraction recovery of catalyst and ligand does not recycle most of the $ZnCl_2$. Accordingly, the compositions and methods of the present invention avoid the use of a Lewis acid promoter in the hydrocyanation reactions described herein.

In an embodiment, the present invention provides methods and compositions wherein mixtures of the pentenenitriles are used to promote higher nickel catalyst concentrations, rather than using Lewis acid promoters for this purpose. In addition, other alkene compounds, A, can increase the nickel ligand solubility when they are able to bind unto the L-Ni compound to make L-NiA.

As described in greater detail in the Examples, below, compositions containing single and mixed unsaturated organic nitriles we evaluated for their ability to solubilized nickel, in the presence and absence of $ZnCl_2$ in Examples 1-29, and Table 2.

Diphosphite ligand was prepared according to the procedure published in International Application Number PCT/US10/60381, International Application Number PCT/US10/60388, International Application Number PCT/US11/40193. The method of formation also can result in relatively minor quantities of monodentate ligands (7) and (8), shown below, being formed.

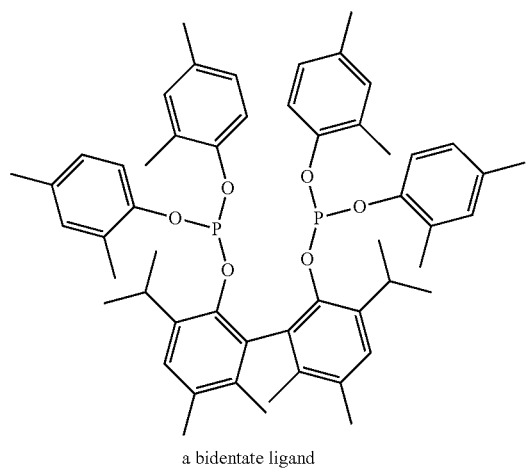

a bidentate ligand (V)

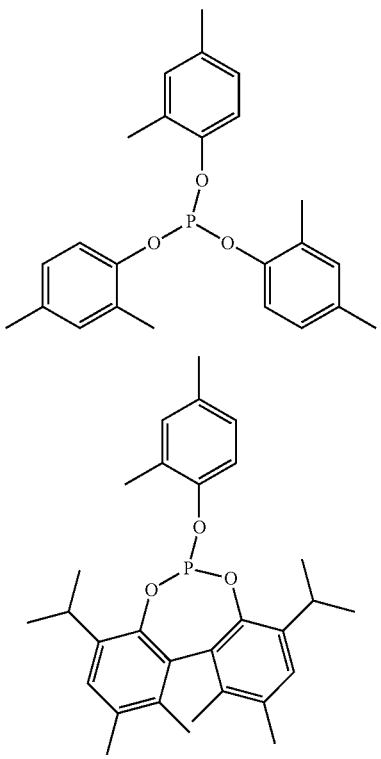

monodentate ligands

Typically, in the industrial hydrocyanation process, the bidentate ligand such as (V) can be used in the presence of minor impurity levels of monodentate ligands such as (7) and (8) that arise from equilibration among the phosphate esters. As is apparent, the monodentate ligands (7) and (8) contain the same phenolic moieties as does (V). The ligand (V) solution can be a mixture in toluene with the major component (exclusive of solvent) being (V), but also including (7), (8), and hydrolysis products of (V), (7), or (8), and other products derived from the compounds used for (V) synthesis.

The bidentate ligand (V) also was evaluated after further removing the monophosphite impurities by removing the toluene solution and crystallizing ligand (V) with methanol solvent. The solid ligand (V) was further purified by crystallization from a toluene and acetonitrile mixture. The ligand (V) without any monophosphites has the same chemistry and results as the mixture as shown in Table 2.

The present invention can provide a method of preparing a catalytic nickel-ligand complex in a solvent composition for a hydrocyanation reaction milieu, comprising contacting nickel metal and a solution of a phosphorus-based ligand in a mixed nitrile solvent composition comprising more than one pentenenitrile, more than one methylbutenenitrile, or a mixture of at least one pentenenitrile and at least one methylbutenenitrile; wherein a concentration of the nickel-ligand complex dissolving in the mixed nitrile solvent composition is increased relative to a concentration of the nickel-ligand complex dissolving in a single nitrile solvent composition comprising a single pentenenitrile or a single methylbutenenitrile, under comparable conditions. For example, the mixture of more than one nitrile can comprise 2-pentenenitrile and 3-pentenenitrile. As discussed above, the phosphorus-based ligand can be ligand of formula (V)

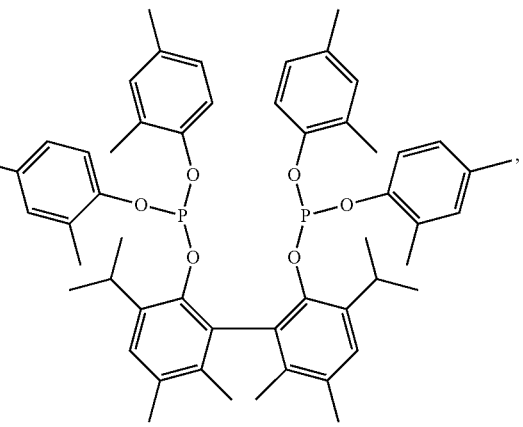

or, of formula (XIII):

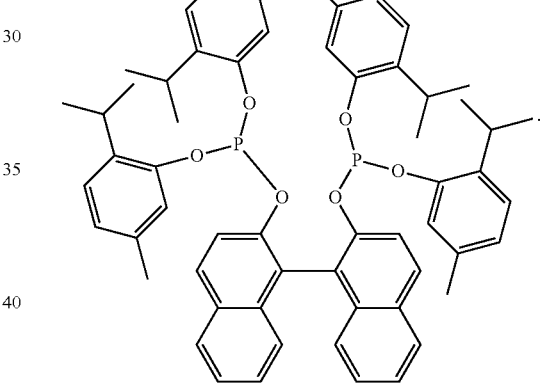

Use of the mixed-nitrile solvent composition can provide a system wherein a concentration of the nickel-ligand complex in the mixed nitrile solvent composition is about 10% higher than a concentration of the nickel-ligand complex in the single nitrile solvent composition under comparable conditions.

Using a method of the invention, a composition comprising a catalytic nickel-ligand complex comprising nickel metal and a solution of a phosphorus-based ligand, in a mixed nitrile solvent composition comprising a mixture comprising more than one pentenenitrile, more than one methylbutenenitrile, or a mixture of at least one pentenenitrile and at least one methylbutenenitrile, can be obtained and used. The mixed nitrile solvent can comprise 2-pentenenitrile and 3-pentenenitrile, both of which can be obtained from the hydrocyanation of butadiene. Again, the phosphorus-based ligand can be ligand (V) or ligand (XIII).

Using a mixed-nitrile solvent composition in which the nickel-ligand complex has been dissolved, a hydrocyanation reaction can be carried out, by a method comprising contacting a hydrocyanation reaction substrate, hydrogen cyanide, and the composition of the invention or prepared by a method of the invention, under conditions suitable to bring about reaction of the substrate and the hydrogen cyanide.

Evaluation of Nickel-Ligand Complex Solubility in Nitrile Solutions

In an exemplary procedure for evaluating the reaction of the ligand (V) at a purity level useful for industrial scale hydrocyanation catalysis, a portion of the toluene can be distilled and (V) ligand mixture subsequently dissolved in cyclohexane. A composition of the (V) ligand solution in cyclohexane can be analyzed by high-performance liquid chromatography (HPLC) analysis. One result obtained is given in Table 1, below.

TABLE 1

| Composition of Ligand (V) | | | |
|---|---|---|---|
| | % wt by HPLC analysis | | |
| | (7) | (8) | (V) |
| V solution | 4.4% | 2.4% | 34.5% |

The ligand (V) also was evaluated after further removing the monophosphite impurities by removing the toluene solution and crystallizing ligand (V) with methanol solvent. The solid ligand (V) was further purified by crystallization from a toluene and acetonitrile mixture. The ligand (V) was greater than 99% purity after filtration and drying.

Diphosphite ligand (XIII) was prepared in a similar manner as diposphite ligand (V) mixture according to the procedure published in International Application Number PCT/US10/60381, International Application Number PCT/US10/60388, International Application Number PCT/US11/40193. The method of formation also can result in relatively minor quantities of monodentate ligands (9) and (10), shown below, being formed. The purity of the diposphite ligand (XIII) mixture was similar to the diphosphite ligand (V) mixture. In addition the diphosphite ligand (XIII) was purified as a solid in a similar manner as ligand (V) described above.

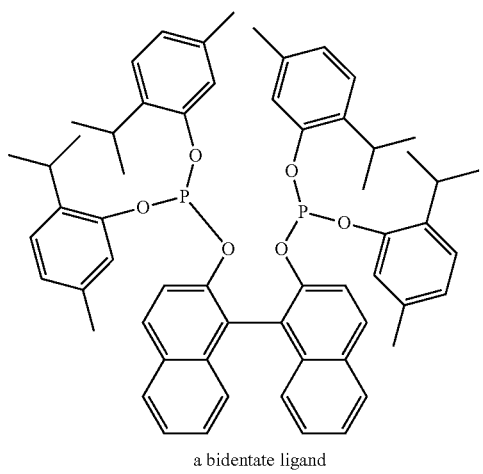

a bidentate ligand (XIII)

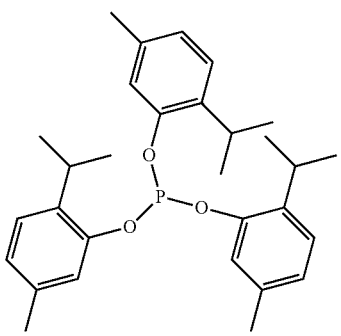

(9)

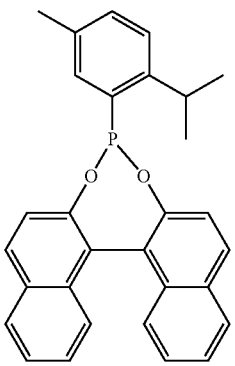

(10)

monodentate ligands

Monodentate phosphite ligands are documented in the prior art and one particular monodentate phosphite ligand was synthesized from a mixture of phenol, meta-cresol and para-cresol in a molar ratio of 1:5:4 respectively. This mixture of aromatic alcohols was reacted with $PCl_3$ as described in prior art to form a mixture of triaryl phosphites (TTP).

Different five carbon unsaturated nitrile isomers, i.e. trans-3-pentenenitrile, cis-2-pentenenitrile, 2-methyl-3-butenenitrile, etc. were obtained by distillation. The concentrations of the nitriles were determined by gas chromatography (GC). $ZnCl_2$ was ACS reagent grade material purchased from Aldrich supplier.

Ni metal suitable for nickel catalyst preparation can be prepared from basic nickel carbonates as described in International Application Number PCT/US10/60381, International Application Number PCT/US10/60388, International Application Number PCT/US11/40193.

The solubilities of the nickel-ligand catalysts in various mixtures, prepared as described for Examples 1-29 in the Examples section, can be determined by treating the nickel metal obtained by a procedure as discussed above, suitable for use in industrial scale hydrocyanation reactions, with the compositions as defined below. Results are shown in Table 2. After contacting the components as disclosed below, the resulting solubilized nickel-ligand levels can be determined by HPLC. A filtered sample of a nickel containing sample can be pre-treated with excess tris(biphenol)diphosphite and heated to stabilize the nickel complex and displace ligand (V) for the analysis by high-performance liquid chromatography (HPLC).

TABLE 2

| | | % wt by GC | | | | | | HPLC Ni ppm$_w$ | By ZnCl$_2$ loading wt. |
| | Time | Cyclo-hexane | 3PN | 4PN | 2PN | 2M3BN | E2M2BN | VN | dissolved in solution | ZnCl$_2$ ppm in solution |
|---|---|---|---|---|---|---|---|---|---|---|
| Example 1 | 24 h | 9.7% | 72.9% | 0.5% | 0.1% | 2.1% | 1.2% | 0.0% | 4220 | 10704 |
| Example 2 | 24 h | 9.6% | 0.3% | 0.0% | 74.0% | 0.0% | 0.0% | 0.0% | 4138 | 10702 |
| Example 3 | 24 h | 9.6% | 36.6% | 0.3% | 38.0% | 1.2% | 0.6% | 0.0% | 4662 | 10702 |
| Example 4 | 24 h | 9.7% | 23.1% | 0.2% | 51.4% | 0.8% | 0.4% | 0.0% | 4638 | 10775 |
| Example 5 | 24 h | 10.2% | 0.3% | 0.0% | 78.0% | 0.0% | 0.0% | 0.0% | 3526 | 10719 |
| Example 6 | 24 h | 9.9% | 38.1% | 0.3% | 39.4% | 1.2% | 0.6% | 0.0% | 4391 | 10646 |
| Example 7 | 24 h | 9.9% | 24.1% | 0.2% | 52.6% | 0.8% | 0.4% | 0.0% | 4411 | 10698 |
| Example 8 | 24 h | 9.1% | 78.0% | 0.9% | 0.6% | 0.8% | 1.2% | 0.0% | 566 | 10423 |
| Example 9 | 24 h | 9.5% | 0.1% | 0.0% | 78.8% | 0.1% | 0.0% | 0.0% | 706 | 10733 |
| Example 10 | 24 h | 9.3% | 42.5% | 0.4% | 37.7% | 0.5% | 0.7% | 0.0% | 597 | 10721 |
| Example 11 | 24 h | 9.2% | 25.0% | 0.3% | 52.9% | 0.4% | 0.4% | 0.0% | 642 | 10719 |
| Example 12 | 24 h | 9.2% | 80.7% | 0.5% | 0.7% | 0.1% | 1.2% | 0.0% | 337 | 0 |
| Example 13 | 24 h | 9.7% | 0.0% | 0.0% | 79.9% | 0.2% | 0.0% | 0.0% | 333 | 0 |
| Example 14 | 24 h | 0.0% | 80.7% | 3.3% | 1.1% | 0.3% | 1.3% | 6.7% | 516 | 9758 |
| Example 15 | 24 h | 0.0% | 64.5% | 0.4% | 0.4% | 0.0% | 1.0% | 0.0% | 11500 | 0 |
| Example 16 | 24 h | 0.0% | 42.8% | 0.3% | 21.9% | 0.0% | 0.6% | 0.0% | 11100 | 0 |
| Example 17 | 24 h | 0.0% | 42.8% | 0.3% | 21.5% | 0.1% | 0.6% | 0.0% | 11500 | 0 |
| Example 18 | 24 h | 0.0% | 0.0% | 0.0% | 0.0% | 0.0% | 0.0% | 65.0% | 11100 | 0 |
| Example 19 | 24 h | 0.0% | 0.0% | 0.0% | 64.7% | 0.2% | 0.0% | 0.0% | 11400 | 0 |
| Example 20 | 24 h | 0.0% | 21.8% | 0.2% | 43.1% | 0.1% | 0.3% | 0.0% | 11300 | 0 |
| Example 21 | 24 h | 0.0% | 20.3% | 0.2% | 42.7% | 0.4% | 0.3% | 0.1% | 11600 | 10603 |
| Example 22 | 24 h | 0.0% | 62.9% | 0.9% | 0.3% | 1.1% | 0.9% | 0.0% | 11600 | 10549 |
| Example 23 | 24 h | 0.0% | 0.1% | 0.0% | 63.3% | 0.1% | 0.0% | 0.1% | 11600 | 10711 |
| Example 24 | 24 h | 10.2% | 0.0% | 0.0% | 0.0% | 0.0% | 0.0% | 80.1% | 180 | 10471 |
| Example 25 | 24 h | 10.1% | 0.0% | 0.0% | 0.0% | 0.0% | 0.0% | 80.5% | 13 | 0 |
| Example 26 | 24 h | 0.0% | 0.0% | 0.0% | 0.0% | 0.0% | 0.0% | 92.8% | 16 | 0 |
| Example 27 | 24 h | 0.0% | 90.9% | 0.3% | 0.0% | 2.6% | 0.0% | 0.0% | 4102 | 10633 |
| Example 28 | 24 h | 9.6% | 0.8% | 0.0% | 76.5% | 0.0% | 0.0% | 0.0% | 2716 | 0 |
| Example 29 | 24 h | 9.7% | 74.5% | 0.5% | 1.9% | 2.2% | 1.7% | 0.0% | 390 | 0 |

3-pentenenitrile (3PN) refers to both trans-3-pentenenitrile and cis-3-pentenenitrile.
E2M2BN refers to Entgegen-2-methyl-2-butenenitrile.
2PN refers to both trans-2-pentenenitrile and cis-2-pentenenitrile,
2M3BN refers to 2-methyl-3-butenenitrile and
VN refers to valeronitrile.

The data presented in Table 2 show that catalyst solutions made from a mixture of pentenenitrile isomers could provide a solution with higher concentration of nickel catalyst compared to pure materials under the same conditions even in the absence of a Lewis acid promoter. Examples 3 and 4 solubilized the nickel as its ligand complex at levels of about 4660 and 4640 ppm respectively, while the single nitrile solvent composition nickel levels were at about 4220 and 4140 ppm respectively, a solubility increase of greater than 10%. Examples 8 and 14 for ligand (XIII) and example 1 and 27 for ligand V show that pure bidentate ligand or mixtures with monophosphites do not make a change in nickel-ligand dissolved. Examples 24-26 compared to examples 1-7 show the critical dependence on unsaturated olefins that can bind to the nickel to form Ligand-Ni-π-allyl-CN—ZnCl2, Ligand-Ni-π-allyl-CN, and Ligand-Ni-olefin complexes and additional other nickel complexes with the unsaturated bond to increase the ligand-catalyst solubility. Examples 15-23 show how monodentate phosphite ligands that are able to form NiL$_4$ complexes do not have the same dependence on the type of nitrile either unsaturated or saturated and on the amount of lewis acid present in order to make the nickel ligand complexes in solution.

Comparison of levels of nickel solubilization between compositions containing mixed pentenenitrile containing compositions free of Lewis acid promoters, and comparable compositions containing Lewis acid promoter zinc chloride, is seen in examples 1-11 and 21-24 (with Lewis acid), versus examples 15-20 (absence of Lewis acids), in various mixed pentenenitrile solvents. Examples 15-20 indicate that high levels of solubilized Ni-ligand complex can be obtained in the mixed pentenenitrile solvent. Surprisingly, the levels of solubilized nickel achieved in the absence of the Lewis acid promoter ZnCl$_2$ in the mixed pentenenitrile systems is at least comparable to solubilized nickel levels observed in the presence of Lewis acid ZnCl$_2$. For instance, comparison of examples 20 (no Lewis acid) and 21 (with Lewis acid), using comparable mixtures of pentenenitriles, indicates that high degree of solubilization of nickel can be achieved in the mixed pentenenitrile solvent wherein a Lewis acid is not present.

EXAMPLES

Example 1: Catalyst Preparation: (V) Ligand Solution with 3-Pentenitrile and ZnCl$_2$ In a nitrogen glove-box, nickel metal, 0.40 g, (V) ligand solution, 1.05 g, ZnCl$_2$, 0.05 g, and 97% pure 3-pentenenitrile, 3.90 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 2: Catalyst Preparation: (V) Ligand Solution with Cis-2-Pentenitrile and ZnCl$_2$ In a nitrogen glove-box, nickel metal, 0.40 g, (V) ligand solution, 1.05 g, ZnCl$_2$, 0.05 g, and 99% pure cis-2-pentenenitrile, 3.90 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 3: Catalyst Preparation: (V) Ligand Solution with Mixture of 3-Pentenenitrile and Cis-2-Pentenitrile and $ZnCl_2$ In a nitrogen glove-box, nickel metal, 0.40 g, (V) ligand solution, 1.05 g, $ZnCl_2$, 0.05 g, 99% pure cis-2-pentenenitrile, 1.96 g, and 97% 3-pentenenitrile, 1.96 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 4: Catalyst Preparation: (V) Ligand Solution with Mixture of 3-Pentenenitrile and Cis-2-Pentenitrile and $ZnCl_2$ In a nitrogen glove-box, nickel metal, 0.40 g, (V) ligand solution, 1.05 g, $ZnCl_2$, 0.05 g, 99% pure cis-2-pentenenitrile, 2.65 g, and 97% 3-pentenenitrile, 1.25 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 5: Catalyst Preparation: (V) Ligand Solution with Trans-2-Pentenitrile and $ZnCl_2$ In a nitrogen glove-box, nickel metal, 0.40 g, (V) ligand solution, 1.05 g, $ZnCl_2$, 0.05 g, 99% pure trans-2-pentenenitrile, 3.90 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 6: Catalyst Preparation: (V) Ligand Solution with Mixture of 3-Pentenenitrile and Trans-2-Pentenitrile and $ZnCl_2$ In a nitrogen glove-box, nickel metal, 0.40 g, (V) ligand solution, 1.05 g, $ZnCl_2$, 0.05 g, 99% pure trans-2-pentenenitrile, 1.95 g, and 97% 3-pentenenitrile, 1.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 7: Catalyst Preparation: (V) Ligand Solution with Mixture of 3-Pentenenitrile and Trans-2-Pentenitrile and $ZnCl_2$ In a nitrogen glove-box, nickel metal, 0.40 g, (V) ligand solution, 1.05 g, $ZnCl_2$, 0.05 g, 99% pure trans-2-pentenenitrile, 2.65 g, and 97% 3-pentenenitrile, 1.26 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 8: Catalyst Preparation: (XIII) Ligand Solution with 3-Pentenenitrile and $ZnCl_2$ In a nitrogen glove-box, nickel metal, 0.40 g, (XIII) ligand solution, 1.05 g, $ZnCl_2$, 0.05 g, and 97% 3-pentenenitrile, 3.90 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 9: Catalyst Preparation: (XIII) Ligand Solution with Trans-2-Pentenitrile and $ZnCl_2$ In a nitrogen glove-box, nickel metal, 0.40 g, (XIII) ligand solution, 1.05 g, $ZnCl_2$, 0.05 g, and 99% pure cis-2-pentenenitrile, 3.92 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 10: Catalyst Preparation: (XIII) Ligand Solution with Mixture of 3-Pentenenitrile and Cis-2-Pentenitrile and $ZnCl_2$ In a nitrogen glove-box, nickel metal, 0.40 g, (XIII) ligand solution, 1.05 g, $ZnCl_2$, 0.05 g, 99% pure cis-2-pentenenitrile, 1.62 g, and 97% 3-pentenenitrile, 2.07 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 11: Catalyst Preparation: (XIII) Ligand Solution with Mixture of 3-Pentenenitrile and Cis-2-Pentenitrile and $ZnCl_2$ In a nitrogen glove-box, nickel metal, 0.40 g, (XIII) ligand solution, 1.05 g, $ZnCl_2$, 0.05 g, 99% pure cis-2- pentenenitrile, 2.65 g, and 97% 3-pentenenitrile, 1.25 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 12: Catalyst Preparation: (XIII) Ligand Solution with 3-Pentenenitrile

In a nitrogen glove-box, nickel metal, 0.40 g, (XIII) ligand solution, 1.05 g and 97% 3-pentenenitrile, 3.91 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 13: Catalyst Preparation: (XIII) Ligand Solution with Cis-2-Pentenitrile In a nitrogen glove-box, nickel metal, 0.40 g, (XIII) ligand solution, 1.05 g and 99% pure cis-2-pentenenitrile, 3.96 g, were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 14: Catalyst Preparation: (XIII) Ligand with 3-Pentenenitrile and $ZnCl_2$ In a nitrogen glove-box, nickel metal, 0.40 g, 98% pure (XIII) ligand, 0.37 g, $ZnCl_2$, 0.05 g, 97% 3-pentenenitrile, 4.60 g, and 99% valeronitrile, 0.35 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 15: Catalyst Preparation: TTP Ligand with 3-Pentenenitrile

In a nitrogen glove-box, nickel metal, 0.40 g, 99% TTP ligand, 1.72 g and 97% 3-pentenenitrile, 3.32 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 16: Catalyst Preparation: TTP Ligand with Mixture of 3-Pentenenitrile and Trans-2-Pentenenitrile In a nitrogen glove-box, nickel metal, 0.40 g, TTP ligand, 1.72 g and 99% pure trans-2-pentenenitrile, 1.11 g, and 97% 3-pentenenitrile, 2.20 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 17: Catalyst Preparation: TTP Ligand with Mixture of 3-Pentenenitrile and Cis-2-Pentenitrile In a nitrogen glove-box, nickel metal, 0.40 g, TTP ligand, 1.72 g, 99% pure cis-2-pentenenitrile, 1.11 g, and 97% 3-pentenenitrile, 2.21 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 18: Catalyst Preparation: TTP Ligand with Valeronitrile

In a nitrogen glove-box, nickel metal, 0.40 g, TTP ligand, 1.72 g and 99% valeronitrile, 3.30 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol) diphosphite and heat to stabilize the nickel complex during the analysis by LC, Table 2.

Example 19: Catalyst Preparation: TTP Ligand with Cis-2-Pentenenitrile

In a nitrogen glove-box, nickel metal, 0.40 g, TTP ligand, 1.71 g and 99% pure cis-2-pentenenitrile, 3.31 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 20: Catalyst Preparation: TTP Ligand with Mixture of Cis-2-Pentenenitrile and 3-Pentenenitrile In a nitrogen glove-box, nickel metal, 0.40 g, TTP ligand, 1.71 g, 99% pure cis-2-pentenenitrile, 2.22 g, and 97% 3-pentenenitrile, 1.10 g, were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 21: Catalyst Preparation: TTP Ligand with Mixture of Cis-2-Pentenenitrile and 3-Pentenenitrile and $ZnCl_2$ In a nitrogen glove-box, nickel metal, 0.40 g, TTP ligand, 1.71 g, $ZnCl_2$, 0.05 g, 99% pure cis-2-pentenenitrile, 2.22 g, and 97% 3-pentenenitrile, 1.06 g, were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 22: Catalyst Preparation: TTP Ligand with 3-Pentenenitrile and $ZnCl_2$

In a nitrogen glove-box, nickel metal, 0.40 g, TTP ligand, 1.71 g, $ZnCl_2$, 0.05 g, and 97% 3-pentenenitrile, 3.25 g, were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 23: Catalyst Preparation: TTP Ligand with Cis-2-Pentenenitrile and $ZnCl_2$ In a nitrogen glove-box, nickel metal, 0.40 g, TTP ligand, 1.71 g, $ZnCl_2$, 0.05 g, and 99% pure cis-2-pentenenitrile, 3.25 g, were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 24: Catalyst Preparation: (V) Ligand Solution with Valeronitrile and $ZnCl_2$ In a nitrogen glove-box, nickel metal, 0.40 g, (V) ligand solution, 1.06 g, $ZnCl_2$, 0.05 g and 99% pure valeronitrile, 3.91 g, were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 25: Catalyst Preparation: (V) Solution with Valeronitrile

In a nitrogen glove-box, nickel metal, 0.40 g, (V) ligand solution, 1.05 g, and 99% pure valeronitrile, 3.96 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 26: Catalyst Preparation: (V) Ligand with Valeronitrile

In a nitrogen glove-box, nickel metal, 0.40 g, 99% pure (V) ligand solution, 0.37 g, $ZnCl_2$, 0.05 g, and 99% pure valeronitrile, 4.65 g, were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 27: Catalyst Preparation: (V) Ligand with 3-Pentenenitrile and $ZnCl_2$

In a nitrogen glove-box, nickel metal, 0.40 g, 99% pure (V) ligand, 0.36 g, $ZnCl_2$, 0.05 g, and 97% 3-pentenenitrile, 4.61 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 28: Catalyst Preparation: (V) Ligand Solution with Cis-2-Pentenitrile

In a nitrogen glove-box, nickel metal, 0.40 g, (V) ligand solution, 1.05 g, and 99% pure cis-2-pentenenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

Example 29: Catalyst Preparation: (V) Ligand Solution with 3-Pentenenitrile

In a nitrogen glove-box, nickel metal, 0.40 g, (V) ligand solution, 1.05 g, and 97% 3-pentenenitrile, 3.95 g were combined in a 10 ml serum bottle sealed with a Teflon lined septum. The solution was stirred with a magnetic stirrer at 65° C. for 24 hours to obtain a nickel catalyst solution. The amount of nickel in solution was measured by high-performance liquid chromatography after pre-treating with excess tris(biphenol)diphosphite and heat to stabilize the nickel complex during the analysis by LC, Table 2.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of preparing a composition comprising a catalytic ML$_2$A-type nickel-ligand complex, the method comprising:

contacting a nickel metal and a solution of a bidentate phosphorus-based ligand in a mixed unsaturated nitrile solvent system comprising more than one pentenenitrile, more than one methylbutenenitrile, or a mixture of at least one pentenenitrile and at least one methylbutenenitrile, in the absence of a Lewis acid promoter, to form the composition comprising the catalytic ML$_2$A-type nickel ligand complex;

wherein

M is nickel metal, L$_2$ is a single mole equivalent of a bidentate phosphorus-based ligand, and A is an unsaturated compound, and the ML$_2$A-type nickel-ligand complex is dissolved in the mixed unsaturated nitrile solvent system.

2. The method of claim 1 wherein the mixed unsaturated nitrile solvent system comprises at least any two of 2-pentenenitrile and 3-pentenenitrile and 2-methyl-3-butanenitrile and 2-methyl-2-butenenitrile and 4-pentenenitrile.

3. The method of claim 1 wherein the mixed nitrile solvent comprises a mixture of about one part 2-penetenenitrile and two parts 3-pentenenitrile by weight.

4. The method of claim 1, wherein the mixed unsaturated nitrile solvent system is at least in part from a recycle stream of a hydrocyanation reaction process for adiponitrile production.

5. The method of claim 1, wherein at least some of the mixture of unsaturated nitriles is from a recycle stream in a hydrocyanation reaction process.

6. The method of claim 1 wherein the bidentate ligand is of formula (XII)

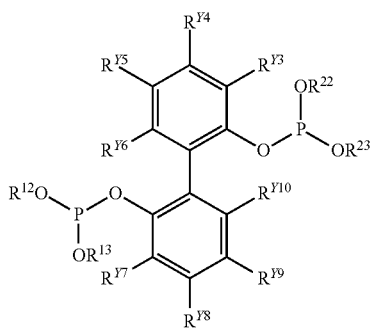

(XII)

wherein R$^{12}$, R$^{13}$, R$^{22}$ and R$^{23}$ are each independently an unsubstituted or a substituted monovalent aryl, and each of R$^{Y3}$-R$^{Y10}$ is independently selected from the group consisting of hydrogen, (C$_1$-C$_{10}$) alkyl, and (C$_1$-C$_{10}$)alkoxy, or wherein two adjacent R$^{Y3}$-R$^{Y10}$ groups together form an optionally substituted fused aryl ring.

7. The method of claim 6, wherein R$^{12}$, R$^{13}$, R$^{22}$, and R$^{23}$ are each independently phenyl substituted at a respective single ortho-position with a (C$_1$-C$_{10}$)alkyl or (C$_1$-C$_{10}$) alkoxy, wherein respective meta- and para-positions of the R$^{12}$, R$^{22}$, R$^{22}$, and R$^{23}$ phenyls can each independently be unsubstituted or be independently substituted with (C$_1$-C$_{10}$) alkyl, (C$_3$-C$_{10}$)cycloalkyl, (C$_1$-C$_{10}$)alkoxy, (C3-C$_{10}$)cycloalkoxy, (C$_3$-C$_{10}$)cycloalkyl(C$_1$-C$_{10}$)alkyl, (C$_3$-C$_{10}$)cycloalkoxy(C$_1$-C$_{10}$)alkyl, (C3-C$_{10}$)cycloalkyl(C$_1$-C$_{10}$) alkoxy, or (C$_3$-C$_{10}$)cycloalkoxy(C$_1$-C$_{10}$)alkoxy;

R$^{Y6}$ and R$^{Y10}$ are independently (C$_1$-C$_{10}$)alkyl or (C$_1$-C$_{10}$) alkoxy, and R$^{Y3}$, R$^{Y4}$, R$^{Y5}$, R$^{Y7}$, R$^{Y8}$, and R$^{Y9}$, are independently H, (C$_1$-C$_{10}$)alkyl, or (C$_1$-C$_{10}$)alkoxy, provided that at least one of R$^{Y3}$, R$^{Y4}$, or R$^{Y5}$, and at least one of R$^{Y7}$, R$^{Y8}$, or R$^{Y9}$, is (C$_1$-C$_{10}$)alkyl or (C$_1$-C$_{10}$)alkoxy.

8. The method of claim 1, wherein the bidentate ligand is of formula (V):

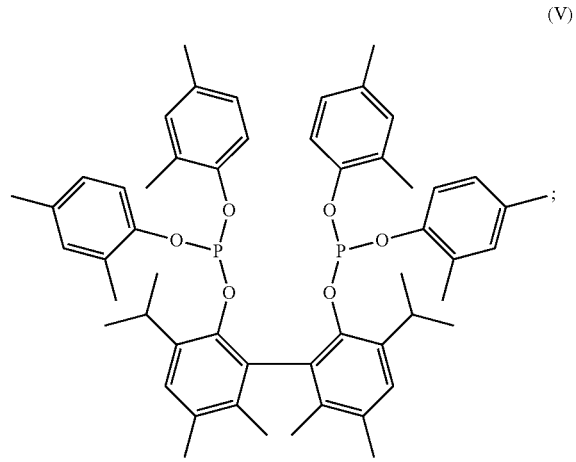

(V)

or is of formula (XIII):

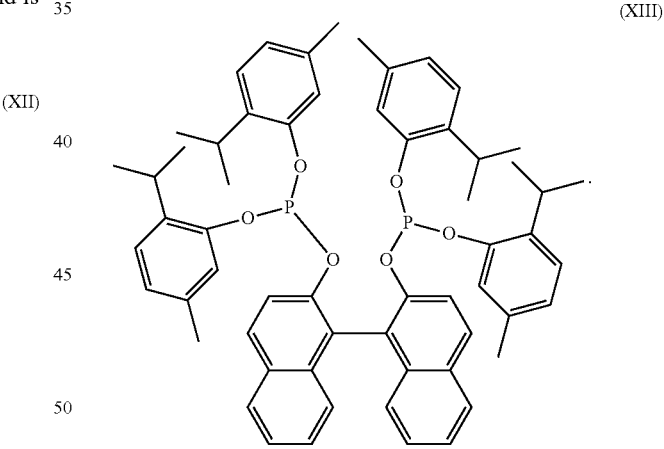

(XIII)

9. The method of claim 1, wherein a concentration of the nickel-ligand complex dissolved in the mixed nitrile solvent composition is greater than a concentration of the nickel-ligand complex dissolved in a single nitrile solvent composition comprising a single pentenenitrile or a single methylbutenenitrile, under comparable conditions.

10. The method of claim 1 wherein a concentration of the nickel-ligand complex in the mixed nitrile solvent composition is greater than a concentration of the nickel-ligand complex in a single unsaturated nitrile solvent, under comparable conditions.

11. The method of claim 1 wherein the concentration of the nickel-ligand complex in the mixed nitrile solvent is at least about 5% higher than can be achieved for the nickel-ligand complex under comparable conditions in a single unsaturated nitrile solvent, under comparable conditions.

12. The method of claim 1, wherein the nickel metal and the bidentate phosphorus-based ligand in the mixed unsaturated nitrile solvent composition are contacted at a temperature of 25-70° C.

13. The method of claim 1, further comprising:
placing the composition comprising the catalytic $ML_2A$-type nickel-ligand complex, butadiene, and hydrogen cyanide contained in a reactor suitable for carrying out a hydrocyanation reaction, to form a hydrocyanation reaction milieu, the reaction milieu being free of a Lewis acid promoter.

14. The method of claim 13, further comprising:
recharging the hydrocyanation reaction milieu during a hydrocyanation reaction process with a recharge solvent system comprising the $ML_2A$-type nickel-ligand complex, the recharge solvent system comprising a mixture of unsaturated nitriles, the mixture comprising more than one pentenenitrile, more than one methylbutenenitrile, or a mixture of at least one pentenenitrile and at least one methylbutenenitrile.

15. The method of claim 14, wherein at least a portion of the recharge solvent system comprising the mixture of unsaturated nitriles is from a recycle stream of a hydrocyanation reaction process.

16. The method of claim 1, further comprising:
carrying out a hydrocyanation reaction, comprising contacting an unsaturated hydrocyanation reaction substrate, hydrogen cyanide, and the composition comprising a catalytic $ML_2A$-type nickel-ligand complex, under conditions suitable to bring about reaction of the substrate and the hydrogen cyanide.

17. The method of claim 16, wherein the unsaturated hydrocyanation reaction substrate is the unsaturated compound A.

18. The method of claim 16 wherein the unsaturated hydrocyanation reaction substrate comprises at least any two of 2-pentenenitrile and 3-pentenenitrile and 2-methyl-3-butanenitrile and 2-methyl-2-butenenitrile and 4-pentenenitrile.

19. The method of claim 16 wherein the mixed nitrile solvent comprises a mixture of about one part 2-pentenenitrile and two parts 3-pentenenitrile by weight.

20. The method of claim 16 wherein the conditions comprise a reaction temperature of 80-140° C.

21. The method of claim 16, wherein the $ML_2A$-type nickel-ligand complex in a solvent system comprising a mixture of unsaturated nitriles is prepared using a recycle stream from a hydrocyanation reaction.

* * * * *